(12) United States Patent
Wang et al.

(10) Patent No.: US 9,180,154 B2
(45) Date of Patent: Nov. 10, 2015

(54) METHOD OF MANUFACTURING MAGNOLIIDAE COMPOUNDS

(75) Inventors: Yibing Wang, Chandler, AZ (US); Peter J. Reilly, Scottsdale, AZ (US)

(73) Assignee: Arizona Health Consulting Group, LLC, Tempe, AZ (US)

( * ) Notice: Subject to any disclaimer, the term of this patent is extended or adjusted under 35 U.S.C. 154(b) by 831 days.

(21) Appl. No.: 12/612,966

(22) Filed: Nov. 5, 2009

(65) Prior Publication Data
US 2011/0104310 A1 May 5, 2011

(51) Int. Cl.
A61K 36/57 (2006.01)
(52) U.S. Cl.
CPC ........................................ A61K 36/57 (2013.01)
(58) Field of Classification Search
CPC ........... A61K 36/57; A61K 36/00; A61P 3/04
See application file for complete search history.

(56) References Cited

U.S. PATENT DOCUMENTS

| | | | |
|---|---|---|---|
| 6,555,074 B1 | 4/2003 | Sweet | |
| 6,582,735 B2 * | 6/2003 | Stogniew et al. | |
| 7,138,134 B2 * | 11/2006 | Wang et al. | |
| 2003/0113389 A1 | 6/2003 | Wang et al. | |
| 2004/0156932 A1 | 8/2004 | Wu | |
| 2008/0081781 A1 * | 4/2008 | Lippa et al. | |
| 2008/0171096 A1 * | 7/2008 | Wu | |
| 2009/0048246 A1 | 2/2009 | Liu et al. | |

FOREIGN PATENT DOCUMENTS

| | | | |
|---|---|---|---|
| CN | 1814177 A * | 8/2006 |
| JP | 62012777 A * | 1/1987 |
| KR | 2003083348 A * | 10/2003 |
| KR | 2005082446 A * | 8/2005 |

OTHER PUBLICATIONS http://www.britannica.com/EBchecked/topic/357583/Magnoliidae. Magnoliidae (plant subclass)—Britannica Online Encyclopedia. Downloaded from word-wide-web on Apr. 1, 2012.*
Wu, J. Neuroscience Letters vol. 222, Issue 2, Jan. 31, 1997, pp. 115-118. Tetrahydroberberine inhibits acetylcholine-induced induced K+ current in acutely dissociated rat hippocampal CA1 pyramidal neurons.*
Inbaraj, JJ et al.Chem. Res. Toxicol., 2006, 19 (6), pp. 739-744. Photochemistry and Photocytotoxicity of Alkaloids from Goldenseal (*Hydrastis canadensis* L.). 2. Palmatine, Hydrastine, Canadine, and Hydrastinine.*
Brezova, W et al.Phytotherapy Research vol. 18, Issue 8, pp. 640-646, Aug. 2004. Oxygen activation by photoexcited protoberberinium alkaloids from Mahonia aquifolium.*
http://en.wikipedia.org/wiki/Chemical_compound. Wikipedia, "Chemical compounds". Downloaded from www 28JAN2013-NPL.*
http://en.wikipedia.org/wiki/List_of_compounds. Wikipedia, "List of compounds". Downloaded from www 28JAN2013-NPL.*
http://en.wikipedia.org/wiki/Alkaloid. Wikipedia, "Alkaloid". Downloaded from www 28JAN2013-NPL.*
12612966-STN_CAS Registry Search History-28JAN2013.*
Yang, Z et al. Proc. Intl. Soc. Mag. Reson. Med. 14(2006). L-Tetrahydropalmatine induces a negative BOLD signal in the nucleus accumbens and orbitofronal cortex in herion-dependent rats.*
Astrup et al., "Randomized Controlled Trials of the D1/D5 Antagonist Ecopipam for Weight Loss in Obese Subjects", Obesity, vol. 15, No. 7, pp. 1717-1731, Jul. 2007.
Kechun Yang et al. "The Neuropharmacology of (-)- Stepholidine and it's Potential Applicaions" Current Neuropharmacology, vol. 5, No. 4, 2007, pp. 289-294.
Cosyns J P et al. "Urothelial Lesions in Chinese-herb nephropathy", American Journal of Kidney Diseases, W.B. Suanders, Philidelphia, PA, US, vol. 33, No. 6,Jun. 1, 1999, pp. 1011-1017.
Database Biosis, Niwa M. et al: Dopaminergic Unique Affinity of Tetrahydroberberine and L Tetrahydroberbernie-D-Camphor Sulfonate Biosciences Information Services, Philadelphia, PA, US, vol. 43, No. 6, 1991, pp. 329-336.
De Broe et al: "On a nephrotoxic and carcinogenic slimming regimen", American Journal of Kidney Diseases, W.B. Saunders, Philadelphia, PA, US, vol. 33, No. 6, Jun. 1, 1999, pp. 1171-1173.
Kerry Bone: "Endangered Herbs—Seeking Out Alternatives", Modern Phytotherapist, vol. 2, No. 3, Jan. 1, 1996, pp. 1-39, *p. 7-p. 8.
J-L. Vanherweghem et al: "Rapidly Progressive Interstitial Renal Fibrosis in Young Women: Association with Slimming Regimen Including Chinese Herbs", The Lancet, vol. 341, No. 8842, Feb. 1, 1993, pp. 387-391.
Database WPI, Week 200654, Thomas Scientific, London, GB; AN 2006-526374, KR 2005082446 A (MD Bioalpha), Aug. 24, 2005, Abstract.

* cited by examiner

*Primary Examiner* — Michele Flood
(74) *Attorney, Agent, or Firm* — Robert D. Atkins; Atkins and Associates, P.C.

(57) ABSTRACT

Magnoliidae compounds are made by obtaining parts of Magnoliidae plants. The parts of the Magnoliidae plants are mixed with alcohol and water. The mixture of the parts of the Magnoliidae plants, alcohol and water is heated and the parts of the Magnoliidae plants are removed so that a liquid mixture remains. The liquid mixture is drying to form a solid composition. Alcohol and water are added to the solid composition to reconstitute the solid composition into a liquid composition. The liquid composition is heated to form solid matter. The solid matter is dried to obtain a purified composition of the Magnoliidae compounds. A dose of Magnoliidae compounds promotes weight loss and can be administered in liquid form, sublingually, intravenously, in a pharmaceutically acceptable carrier, in combination with a metabolite detoxification agent, in combination with a nutritional or dietary supplement, or in chewing gum.

23 Claims, 6 Drawing Sheets

METHOD OF MANUFACTURING MAGNOLIIDAE COMPOUNDS

FIELD OF THE INVENTION

The present invention relates in general to a method for decreasing a person's appetite in order to assist in weight loss, and more specifically, to a method for decreasing a person's appetite by treating the person with a class of natural compounds such as tetrahydroberberine (THB) and its analogs, isolated from the Magnoliidae superorder of plants, such as *Corydalis* and *Stephania*.

BACKGROUND OF THE INVENTION

Obesity is defined as a body mass index of greater than 30, whereas overweight is defined as having a body mass index of greater than 25. Approximately 19% of Americans are obese, and 35% are overweight. The incidence of being overweight and obese has increased dramatically in the last decade. In the United States, over $33 billion are spent each year for weight loss products ($0.5 billion alone on drugs) with 14% of adults using prescription drugs for weight loss and 7% using over the counter drugs.

Obesity involves multiple factors that contribute to the disease, including genetic, metabolic, psychosocial, lifestyle, nutrition, exercise, and environmental factors. The great majority of obesity cases are probably due to a complex relationship between the many factors which regulate energy intake and utilization. Obesity is a life-long disorder with adverse health consequences. Obesity is considered the second leading cause of death in the United States and contributes to at least 300,000 deaths per year. It is associated with a number of diseases, including diabetes (80% of type II diabetics are obese), hypertension, gallstones, respiratory problems, and mortality rates for certain types of cancers.

Given the large obese population and the associated problems, the area of obesity research and product development for the management of obesity has been extensively explored, yet the problem remains. The currently available weight management programs almost all take a lifetime commitment by the patients and involve painful lifestyle changes.

Many known pharmaceutical agents designed for weight loss and fat loss have notable side effects. For example, the side effects of adrenergic agents include insomnia, nervousness, irritability, headache, nausea, and constipation. Some adrenergic agents can even increase blood pressure and precipitate angina. The side effects of lipase inhibitors include nausea, vomiting, abdominal pain, oily spotting, fatty oily stool, flatus, fecal urgency, increased defecation, and fecal incontinence. The gastrointestinal side effects could be worse if dietary fat is not reduced. Sibutramine can cause headache, insomnia, constipation, and dry mouth, as well as an increase in blood pressure and pulse rate. Agents that increase energy expenditure such as ephedrine, theophylline, and thyroid hormone carry the risk of cardiac complications from hypertension and increased heart rate. Cholecystokinin is a peptide that activates gastric vagal fibers, and triggers satiety. However, it must be administered parenterally, dramatically limiting its use. Serotonergic agents have been withdrawn from the market after valvular heart disease was reported in patients using the combination of fenfluramine and phentermine.

SUMMARY OF THE INVENTION

In one embodiment, the present invention is a method of manufacturing Magnoliidae compounds comprising the steps of obtaining parts of Magnoliidae plants, and mixing the parts of the Magnoliidae plants with alcohol and water, followed by heating the mixture of the parts of the Magnoliidae plants, alcohol, and water. The method further includes the steps of removing the parts of the Magnoliidae plants such that a liquid mixture remains, drying the liquid mixture to form a solid composition, adding alcohol and water to the solid composition to reconstitute the solid composition into a liquid composition, heating the liquid composition to form solid matter, and drying the solid matter to obtain a purified composition of the Magnoliidae compounds.

In another embodiment, the present invention is a pharmaceutical composition comprising a mixture of herbal extracts from Magnoliidae plants as an active ingredient and a pharmaceutically acceptable carrier for assisting in weight loss in a human.

In another embodiment, the present invention is a method of reducing body weight and body fat in a human, which comprises the step of administering a dose of Magnoliidae compounds to the human to reduce the human's weight. The dose of Magnoliidae compounds provides an amount greater than 1 milligram/day of the Magnoliidae compounds.

In another embodiment, the present invention is a pharmaceutical composition comprising a mixture of herbal extracts from Magnoliidae plants as an active ingredient and a pharmaceutically acceptable carrier for facilitating weight loss in a human. The mixture of herbal extracts includes at least 1% THB and at least 1% THP based on the total weight of the pharmaceutical composition.

Other independent features and advantages of the method for decreasing body weight and body fat in living organisms will become apparent from the following detailed description, taken in conjunction with the accompanying drawings which illustrate, by way of example, the principles of the invention.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

The following description presents a method for reducing appetite by treating a human with one of a group of chemical analogs isolated from the Magnoliidae superorder of plants.

Figure 1:
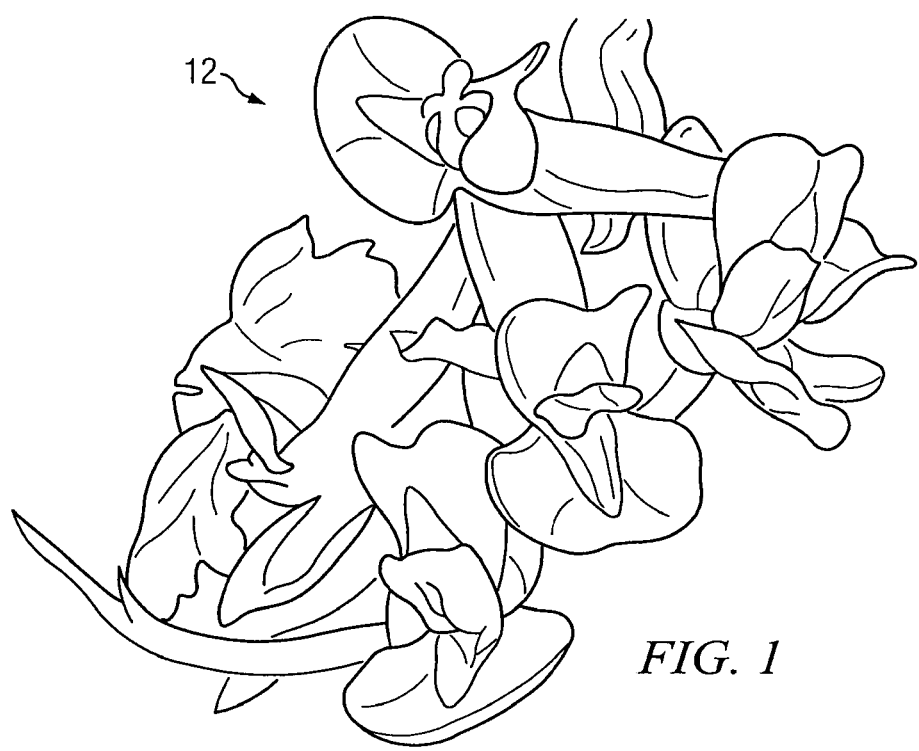
FIG. 1 is an illustration of a *Corydalis ambigua* plant.

FIG. 1 is an illustration of one species of *Corydalis*, specifically, *Corydalis ambigua* 12. *Corydalis ambigua* 12 is one species of the *Corydalis* genus of herbal plants, primarily found in East Asia, namely China, and Japan. Mature *Corydalis ambigua* 12 is about 150.0 cm in height and about 80.0 cm in width. *Corydalis ambigua* 12 is a perennial herb. *Corydalis* is a genus of the Fumariaceae sub-family, the Papaveraceae family, the Papaverales order, and the Magnoliidae superorder of plants.

Figure 2:
FIG. 2 is an illustration of tubers from the *Corydalis ambigua* plant.

FIG. 2 is a depiction of tubers 22 of the *Corydalis ambigua* plant. While one embodiment specifically refers to using the *ambigua* species, any species of *Corydalis* containing THB or its analogs may be used. Thus, the term *Corydalis* refers to all species of *Corydalis* containing THB or its analogs, including *Corydalis ambigua*. Although, one embodiment specifically envisions extracting THB and its analogs from tubers 22 of the *Corydalis ambigua*, THB and its analogs can be extracted by purifying any of the plant parts, including the leaves, stem, and tubers. Furthermore, a second embodiment envisions administering *Corydalis*, without prior purification of THB or its analogs. Thus, the term *Corydalis* encompasses the entire *Corydalis* plant and also all extracts derived from the *Corydalis* plant.

Figure 3A:
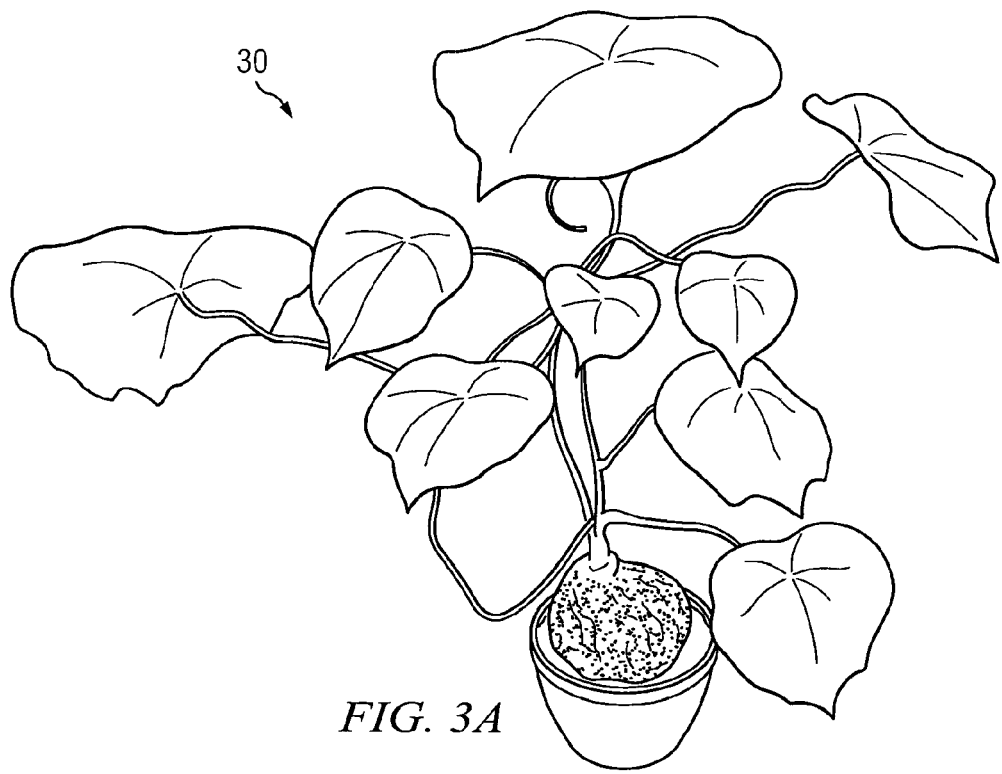
FIGS. 3A-3B are illustrations of a *Stephania* plant and tubers from the *Stephania* plant.
Figure 3B:
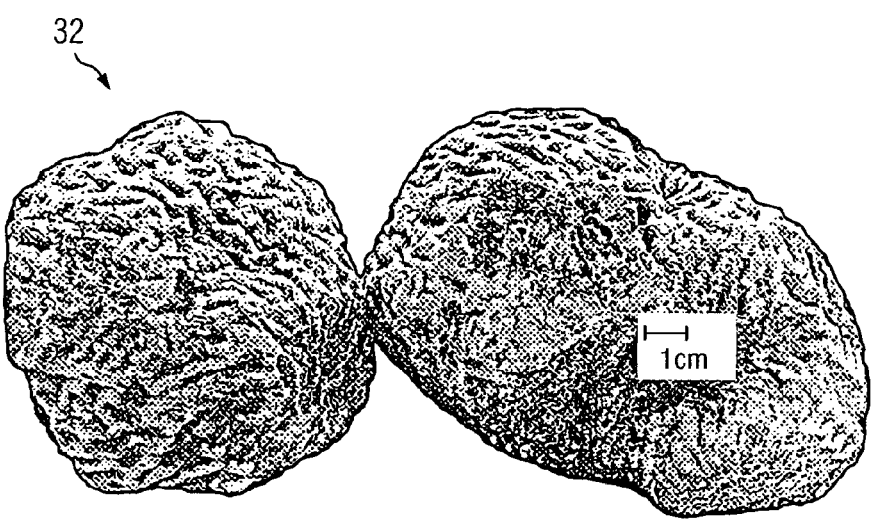

FIG. 3A is an illustration of one species of the *Stephania* genus of plants 30, also a genus of herbal plants, primarily found in East Asia. FIG. 3B is a depiction of tubers 32 of the *Stephania* plant. The *Stephania* genus of plants 30 includes *Stephania intermedia*, *Stephania hainanensis*, and *Stephania yunnanensis*. The *Stephania* genus of plants 30 contains analogs of THB. Specifically, *Stephania intermedia*, *hainanensis*, and *yunnanensis* contain l-tetrahydropalmatine (l-THP or dl-THP) while both *Stephania intermedia* and *yunnanensis* contain l-Stepholidine (l-SPD). L-THP can also be found in and purified from *Fibraurea recisa* Pierre. Both *Stephania* and *Fibraurea* are from the Menispermaceae family and the Ranunculales order of plants. As with *Corydalis*, both *Stephania* and *Fibraurea* belong to the Magnoliidae superorder of plants.

As with *Corydalis*, one embodiment specifically envisions extracting l-THP and l-SPD from the tubers of the *Fibraurea* or *Stephania* plants. In a second embodiment, l-THP and l-SPD can be extracted by purifying any of the plant parts, including the leaves, stem, and tubers. Yet another embodiment envisions administering any species of *Stephania* or *Fibraurea* without prior purification of l-THP or l-SPD.

Figure 4A:
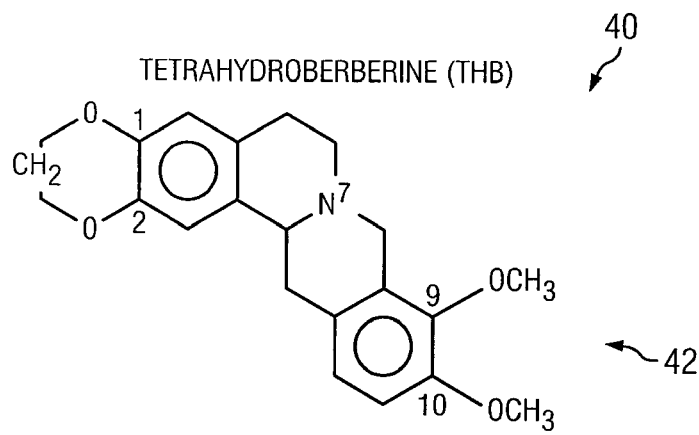
FIGS. 4A-4C show the chemical structure of THB and two analogs of Tetrahydroberberine (THB analogs)
Figure 4B:
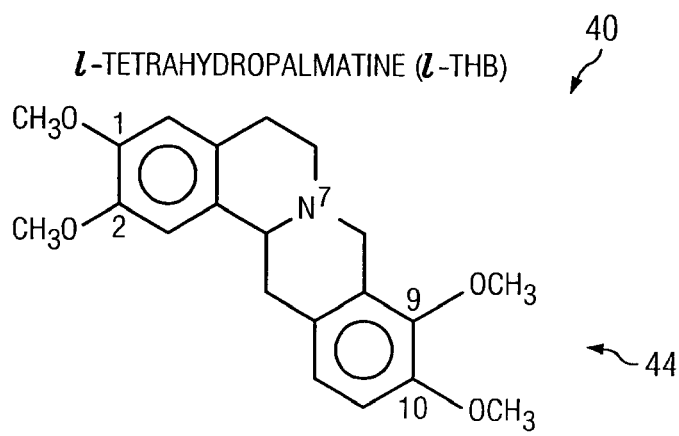
Figure 4C:
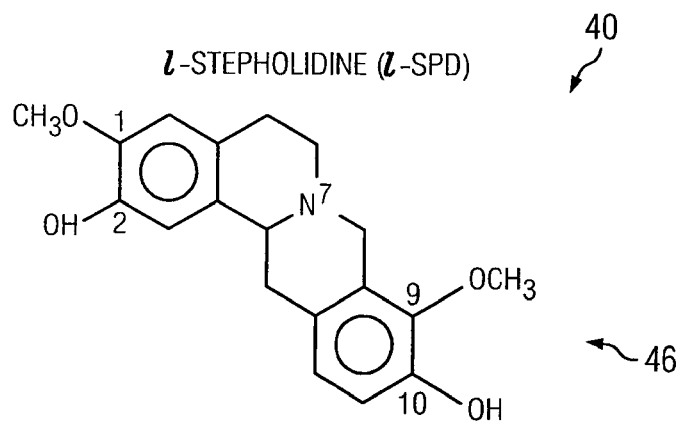

FIGS. 4A-4C show the chemical structure of compounds 40 isolated from Magnoliidae plants. The term Magnoliidae is used to refer to *Corydalis ambigua*, *Stephania intermedia*, *Stephania hainanensis*, *Stephania yunnanensis*, or *Fibraurea recisa* plants that contain THB, l-THP, l-SPD, or any analog of THB, l-THP, or l-SPD. Compounds 40 comprise THB, l-THP, l-SPD, or analog thereof and are referred to herein collectively as "Magnoliidae compounds" or each, singularly, as "a Magnoliidae compound." Magnoliidae compounds 40 also include extracts from *Corydalis ambigua*, *Stephania intermedia*, *Stephania hainanensis*, *Stephania yunnanensis*, or *Fibraurea recisa* plants which contain THB, l-THP, l-SPD, or analog thereof. The analog of Magnoliidae compounds 40 can be characterized by a conserved four-ring structure. For example, the analogs can have a conserved benzene-hexane-hexane-benzene structure, as shown in all Magnoliidae compounds 40.

FIG. 4A shows the chemical structure of THB 42. FIG. 4B shows the chemical structure of one analog of THB 42, l-Tetrahydropalmatine (l-THP) 44. FIG. 4C shows the chemical structure of a second analog of THB 42, l-Stepholidine (l-SPD) 46. l-THP 44 and l-SPD 46 are homolog analogs of THB, and are collectively referred to as "THB analogs." Magnoliidae compounds 40 are extracted from one or more parts of any Magnoliidae species by classical alkaloid chemical purifying method. The Magnoliidae plant is immersed into an alkaline solution, extracted using benzene, then crystallized and purified to get at least one of THB 42, l-THP 44, and l-SPD 46. If Magnoliidae compounds are not practically available as found in or extracted from Magnoliidae plants, Magnoliidae compounds may be synthesized or derived from other sources.

Figure 5A:
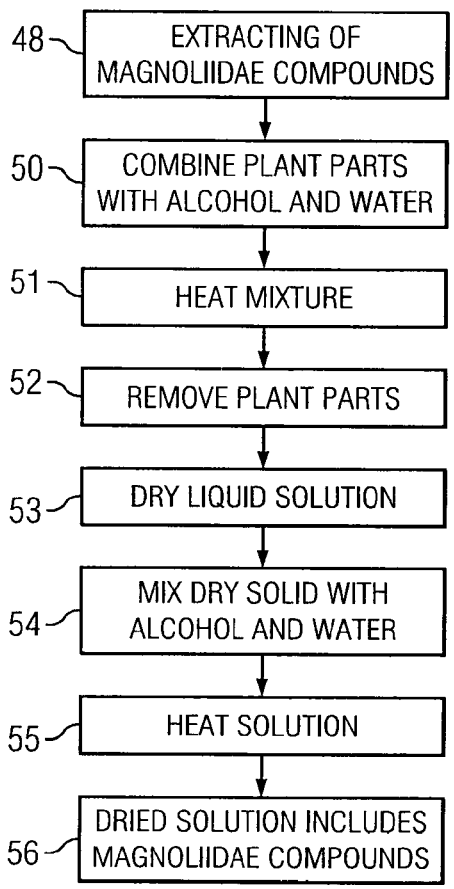
FIGS. 5A-5B show a method of manufacturing Magnoliidae compounds.

As shown in FIG. 5A, the Magnoliidae compounds can be obtained by extracting the Magnoliidae compounds 38 from the tubers, stems, leaves or any other part of the plant. In step 50, the plant parts are combined with alcohol and water in portions depending upon the weight of the plant parts that are used. In step 51, the solution is heated to facilitate the extraction of the Magnoliidae compounds from the plant parts. In step 52, the plant parts are removed from the solution. In step 53, the solution is then dried such that the Magnoliidae compounds are now in solid form, along with other contaminants. In step 54, the dried solid is then mixed with water and alcohol. In step 55, the new solution is then heated to further separate Magnoliidae compounds 40 from other compounds. In step 56, the dried solid contains largely purified, if not completely purified, Magnoliidae compounds 40.

Figure 5B:
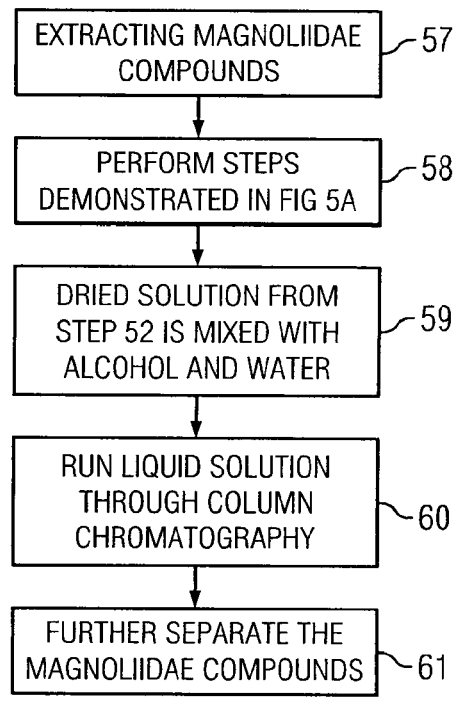

FIG. 5B illustrates another method of manufacturing the Magnoliidae compounds. In step 57, the steps described and illustrated in FIG. 5A are performed. In step 58, the Magnoliidae compounds may be further separated by having the dried solid remixed into solution. In step 59, the liquid solution is run through column chromatography process. In step 60, the column chromatography process further separates the compounds by molecular weight as to further purify Magnoliidae compounds 40. The molecular weight of the Magnoliidae compounds can be determined to obtain the Magnoliidae compounds after being separated by column chromatography.

Although Magnoliidae compounds 40 that are obtained from the natural sources have certain benefits, Magnoliidae compounds 40 can also be formed by chemical synthesis. Magnoliidae compounds 40 can be formed by combining the necessary starter compounds, and performing various chemical reactions to create Magnoliidae compounds 40 from the starter compounds. Additional compounds can be added during the synthesis process to provide the necessary chemical structure to create Magnoliidae compounds 40.

Magnoliidae compounds 40 exhibit a marked depression effect in the central nervous system such as sedation, hypnosis, and analgesia. The pharmacological mechanism of THB and its analogs involve working as a class of antagonists to inhibit brain dopamine (DA) receptor function, blockade of α-adrenergic receptor and 5-TH receptor functions, and direct modulation of ion channel function.

THB and its analogs exhibit all the characteristics of a DA antagonist. Compared with traditional DA receptor antagonists, Magnoliidae compounds 40 exhibit two unique properties. First, THB possesses an equipotent effect on D1-type and D2-type DA receptor binding. Second, in normal rats, l-SPD exhibits the characteristics of D2 receptor antagonist, while in rats with unilateral nigral lesion (DA receptor super sensitivity in striatum), l-SPD acts on D1 receptors as an agonist. Therefore, by blocking DA receptor function, Magnoliidae compounds 40 block dopamine release, which is the major cellular mechanism of reward and dependence.

Figure 6A:
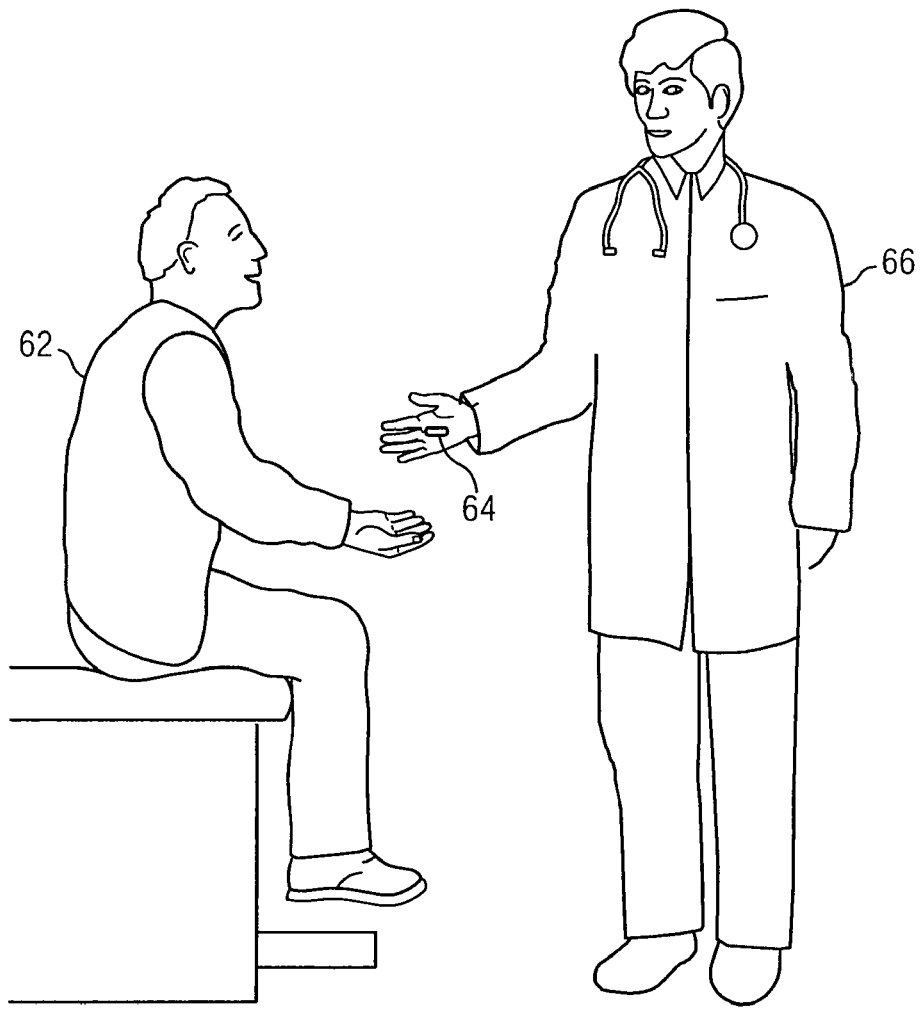
FIGS. 6A-6B show a method of administering Magnoliidae compounds and an illustration of a vessel of administering Magnoliidae compounds.

In FIG. 6A, the method of treating obesity in a human 62 may be through administration of Magnoliidae compounds 40 as a prescription by a medical professional. The administration may be in various formats as described below, including pill 64. Pill 64 may be administered by medical professional 66. Pill 64 can also be obtained over the counter from a retail store. Pill 64 may contain 100% of Magnoliidae compounds 40. In another embodiment, pill 64 may contain acceptable pharmaceutical carriers in some percentage, with the remaining percentage being Magnoliidae compounds 40. For example, pill 64 may have 5% Magnoliidae compounds 40 and 95% acceptable pharmaceutical carriers. The percentages may be varied depending on the intended use of the Magnoliidae compounds 40.

Figure 6B:

In FIG. 6B, the vessel used to administer Magnoliidae compounds 40 may be in the form of capsule 68. Capsule 68 may contain 100% of Magnoliidae compounds 40. Capsule 68 may contain acceptable pharmaceutical carriers in some percentage, with the remaining percentage being Magnoliidae compounds 40. For example, capsule 68 may have 5% Magnoliidae compounds 40 and 95% acceptable pharmaceutical carriers. The percentages may be varied depending on the intended use of the Magnoliidae compounds 40.

Figure 7A:
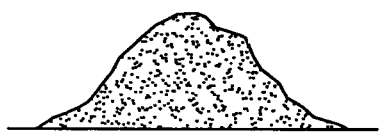
FIGS. 7A-7J are illustrations of vessels administering Magnoliidae compounds.

The method of administration with Magnoliidae compounds 40 can be done in various forms. FIGS. 7A-7J depict various methods of administering the Magnoliidae compounds. The forms may include methods such as mixing the compound with food the human is to consume, prepared in forms of lozenge as in FIG. 7F, tablets as in FIG. 7H, powders as in FIG. 7A, liquids as in FIG. 7C, bars as in FIG. 7G, chewing gum as in FIG. 7B (safe because overdose is unlikely), shakes, candies or other confections, tea bags, or any form of food. Magnoliidae compounds 40 can be administered in a powder form, as shown in FIG. 7A. The advance of powder formulas is that Magnoliidae compounds 40 can easily be mixed with any type of food product and can be administered in a fairly large dosage.

Figure 7B:
Figure 7C:
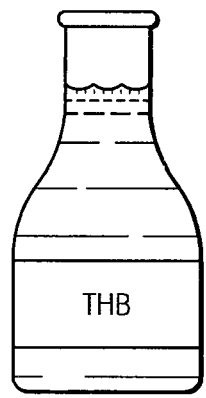
Figure 7D:
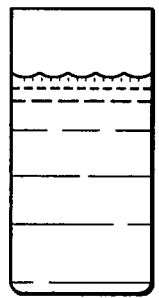
Figure 7E:
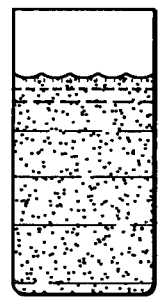
Figure 7F:
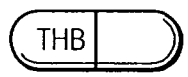

As seen in FIG. 7F, the Magnoliidae compounds 40 may be prepared in lozenge form for ease of portability, as well as ease of ingestion. The amount of active ingredient may vary depending on the necessary dosage. In one embodiment, the lozenge contains 3% THB, 3% THP, and 94% pharmaceutically acceptable carriers. The amount of active THB and THP can vary to allow a higher or lower percentage depending on the desired treatment and the weight of the subject person. For example, the lozenge may contain 100% THB and no pharmaceutically acceptable carriers. The formulation could contain 100% THP as well. For a subject person that is obese, the dosage in the capsule may be increased from 1% THP and/or 1% THB up to 100% of either compound. During the course of treatment, the percentages of each compound may be altered to reach an optimal dosage for the target subject. For example, a lozenge could be created with 15% THB and 10% THP and 75% pharmaceutically acceptable carriers. The amount of THB and THP does not have to be the same. Either THB or THP can have a greater percentage than the other. The amount of each may be dependent on the subject person.

Furthermore, administration of Magnoliidae compounds 40 can be in liquid form, as depicted in FIG. 7C. Magnoliidae compounds 40 can be administered as a drink such as coffee, tea, nutritional and dietary supplement drinks, milk shakes, and protein shakes. A sweetener can be added to the liquid to provide a more appealing taste to the liquid compound. The sweetener may be a natural sugar such as sucrose or could be a synthetic sweetener such as aspartame, saccharin, and acesulfame. The sweeteners may be used to provide a more palatable taste to the liquid as Magnoliidae compounds 40 do not have a very appealing taste, especially in high dosages. The percentages of the Magnoliidae compounds 40 described above for the capsule can be utilized for the administration of Magnoliidae compounds 40 in liquid form.

In FIG. 7B, Magnoliidae compounds 40 may be administered sublingually in the form of chewing gum. The benefits of administering Magnoliidae compounds 40 can be higher safety (not easy to overdose), easy to use (can be chewed any time), easy to adjust the dosage (chewing gum may contain a small unit dosage, such as 0.1 gram Magnoliidae compounds 40 or 1 gram of Magnoliidae compounds 40 per piece), and more targeted use (can be chewed whenever hunger is present). The percentages of Magnoliidae compounds 40 described above for the lozenge can be utilized for the administration of Magnoliidae compounds 40 in the chewing gum.

Figure 7G:
Figure 7H:
Figure 7I:
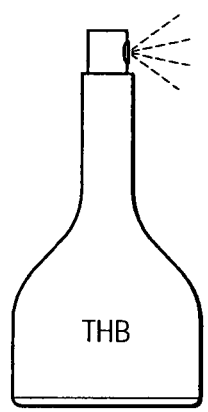

In FIG. 7I, the method of administration of Magnoliidae compounds 40 can also be by integrating the compound into sprays to deliver sublingually to by-pass liver metabolism. The percentages of Magnoliidae compounds 40 described above for the lozenge can be utilized for the administration of Magnoliidae compounds 40 in spray form.

Figure 7J:

In FIG. 7J, the method of administration of Magnoliidae compounds 40 can also be by integrating the compound into injectable forms to deliver parenterally to by-pass liver metabolism and for faster and stronger actions. The percentages of Magnoliidae compounds 40 described above for the lozenge can be utilized for the administration of Magnoliidae compounds 40 in an injectable form.

Alternatively, Magnoliidae compounds 40 be administered in a food bar form, as depicted in FIG. 7G. The dosage form enables the addition of multiple nutrients to ensure adequate intake of essential nutrients, such as vitamins, minerals, and amino acids, to prevent potential malnutrition. The addition of flavors and sweeteners can enhance palatability. It can also be beneficial that Magnoliidae compounds 40 be administered in a shake form. The dosage form enables the addition of multiple nutrients to ensure adequate intake of essential nutrients, such as vitamins, minerals, and amino acids, to prevent potential malnutrition. The addition of flavors and sweeteners can enhance palatability. Yet another preferable way to administer Magnoliidae compounds 40 can be through confections, such as candies. The dosage form can be extremely easy to use due to the high palatability by a wide range of people. The percentages of Magnoliidae compounds 40 described above for the lozenge can be utilized for the administration of Magnoliidae compounds 40 in food form.

Since reduced food intake may lead to reduced nutrient (proteins, carbohydrate, and fatty acids) intake, it can be beneficial to administer Magnoliidae compounds 40 with essential nutrients and nutritional supplements, such as proteins, amino acids, vitamins, macro and trace minerals, or mixture thereof. The addition of other nutritional substances such as creatine can help the body build muscle mass. Furthermore, many nutritional herbs, plant derived phytonutrients, and nutrients from any other sources can be beneficial when administered together with the above mentioned Magnoliidae compounds 40 because they can offer added benefits such as boosting energy, minimizing fatigue, preventing acidosis, increasing metabolic rate, etc. Combining Magnoliidae compounds 40 with proteins may assist in making up lost protein intake due to decreased food intake. One may also mix the combination with the food the person may consume, such as prepared forms of capsules, tablets, powders, liquids, shakes, bars, candies, tea bags, chewing gum or any form of food.

The method of administration of Magnoliidae compounds 40 can also be by combining the compound with a supplemental dose of vitamins to make up for lost vitamin intake due to decreased food intake. One may also mix the combination with the food the person may consume, such as prepared forms of capsules, tablets, powders, liquids, shakes, bars, candies, tea bags, or chewing gum (safe because overdose is unlikely), or any form of food.

The method of administration of Magnoliidae compounds 40 can also be by combining the compound with a supplemental dose of macro and trace minerals to make up for lost mineral intake due to decreased food intake. One may also mix the combination with the food the person may consume, such as prepared forms of capsules, tablets, powders, liquids, shakes, bars, candies, tea bags, chewing gum, or any form of food.

The method of administration of Magnoliidae compounds 40 can also be mixed with a supplemental dose of herbal components to enhance palatability and compliance. One may also mix the combination with the food the person may consume, such as prepared forms of capsules, tablets, powders, liquids, shakes, bars, candies, tea bags, chewing gum, or any form of food.

The method of administration of Magnoliidae compounds 40 can also be by combining the compound with a supplemental dose of creatine to help increase muscle mass. One may also mix the combination with the food the person may consume, such as prepared forms of capsules, tablets, powders, liquids, shakes, bars, candies, tea bags, chewing gum, or any other form of food.

Since reduced food intake may lead to reduced nutrient (proteins, carbohydrate, and fatty acids) intake, it can be beneficial to administer Magnoliidae compounds 40 with essential nutrients or dietary supplements such as proteins, amino acids, vitamins, macro and trace minerals, or the mixture thereof. One may also mix the combination with the food the person may consume, such as prepared forms of capsules, tablets, powders, liquids, shakes, bars, candies, tea bags, chewing gum, or any other form of food.

Furthermore, many herbs, plant derived phytonutrients, and nutrients from any other sources can be beneficial when administered together with the above mentioned Magnoliidae compounds 40 because they can offer added benefits such as boosting energy, minimizing fatigue, preventing acidosis, and increasing metabolic rate.

Other embodiments may involve combining Magnoliidae compounds 40 with metabolite detoxification agents. Adding Calcium D-Glucarate, Potassium Glucarate, or any salt of Glucarate, or Glucaric Acid, as a metabolite detoxification agent, will help the body excrete any toxic metabolites. Detoxification of toxic metabolites assists the body in reducing fat and prevents production of new fatty tissue, as metabolite toxins are primarily stored in a human's fatty tissue.

The following molecules are also effective metabolite detoxification agents: N-Acetyl Cysteine (NAC), Glutathione, Indole-3-Carbinol, Diindoly-3-Methane (DIM), Conjugated Linoleic Acid (CLA), Guanosine Triphosphate (GTP), Selenium, Garlic, Rosox, Milk Thistle (Silymarin), Mixed Vitamin E's, Mixed, Carotenoids, Vitamin C/Bioflavonoids, Lipoic Acid/Dihydrolipoate, Soy Isoflavones, Monoterpenes, Diterpenes, Triperpenes, and Cruciferous Vegetable Sulfur Compounds.

Another embodiment envisions combining Magnoliidae compounds 40 with other weight-reducing agents to develop extra strength formulas or create enhanced weight-reducing compositions that benefit from the unique fat-reducing properties of Magnoliidae compounds 40. Magnoliidae compounds 40 can be combined with other weight-reducing treatments, such as diet, exercise program or other methods used to facilitate weight loss.

The method of achieving weight loss and fat reduction over time comprises administering varying dosages of Magnoliidae compounds 40 over a given period of time. The following illustrations of the weight loss and fat reduction method using Magnoliidae compounds 40 are given as examples to illustrate the use of Magnoliidae compounds 40 to produce weight loss and fat reduction in humans.

The optimal dosage to decrease appetite in a person is by administering a dose of 1-50 mg/Kg of body weight of one or more Magnoliidae compounds 40, including THB, l-THP, l-SPD, or any other THB analog, and the effects can be maintained for 2-3 hours. However, since Magnoliidae compounds 40 easily pass the blood-brain barrier, the compound quickly and easily reaches peak concentration in the brain tissue. Therefore, doses as low as 1 mg/Kg of body weight can cause a decrease in a person's appetite.

Magnoliidae compounds 40 can also be used as a method for aiding sleep. The pharmacological mechanism of Magnoliidae compounds 40 involve working as a class of antagonists to inhibit brain DA receptor function, blockade of α-adrenergic receptor and 5-TH receptor functions, and direct modulation of ion channel function. The antagonist mechanism assists in helping a subject fall asleep and stay asleep. Dopamine release is associated with the reward system in the brain, such that the blockage of dopamine release may assist in limiting the stimulation of the brain in the subject to allow the subject to fall asleep and stay asleep.

Magnoliidae compounds 40 can also be used as a method for treating anxiety. The pharmacological mechanism of Magnoliidae compounds 40 involve working as a class of antagonists to inhibit brain DA receptor function, blockade of α-adrenergic receptor and 5-TH receptor functions, and direct modulation of ion channel function. The antagonist mechanism assists in helping reduce anxiety in a subject. Dopamine release is associated with the reward system in the brain, such that the blockage of dopamine release may assist in limiting the stimulation of the brain in the subject as to allow the subject to experience less anxiety.

While one or more embodiments of the present invention have been illustrated in detail, the skilled artisan will appreciate that modifications and adaptations to those embodiments may be made without departing from the scope of the present invention as set forth in the following claims.

What is claimed is:

1. A method of reducing body weight and body fat in a human comprising administering a dose of tetrahydroberberine (THB), l-tetrahydropalmatine (l-THP), and l-stepholidine (l-SPD) isolated from a *Corydalis ambigua*, a *Stephania intermedia*, a *Stephania hainanensis*, a *Fibraurea recisa*, or a *Stephania yunnanensis* plant to the human to reduce the human's weight, wherein the dose of THB, l-THP, and l-SPD is an amount greater than 1 milligram of a mixture of THB, l-THP, and l-SPD per 1 kilogram of the human.

2. The method of claim 1 comprising administering the dose of THB, l-THP, and l-SPD in liquid form.

3. The method of claim 1 comprising administering the dose of THB, l-THP, and l-SPD sublingually.

4. The method of claim 1 comprising administering the dose of THB, l-THP, and l-SPD intravenously.

5. The method of claim 1 comprising administering the dose of THB, l-THP, and l-SPD in a pharmaceutically acceptable carrier.

6. The method of claim 1 comprising administering the dose of THB, l-THP, and l-SPD in combination with a metabolite detoxification agent.

7. The method of claim 1 comprising administering the dose of THB, l-THP, and l-SPD in combination with a nutritional or dietary supplement.

8. The method of claim 1 comprising administering the dose of THB, l-THP, and l-SPD in chewing gum.

9. A method of reducing body weight and body fat in a human comprising administering to the human a dose of l-tetrahydropalmatine (l-THP) and l-Stepholidine (l-SPD) isolated from a *Corydalis ambigua*, a *Stephania intermedia*, a *Stephania hainanensis*, a *Fibraures recisa*, or a *Stephania yunnanensis* plant in an amount greater than 1 milligram of a mixture of l-THP and l-SPD per 1 kilogram of the human.

10. The method of claim 9 comprising administering the dose of l-THP and l-SPD sublingually, in liquid form, in powder form, in tablet form, in a capsule, in chewing gum, in food, in a lozenge, or in a tea bag.

11. The method of claim 9 comprising administering the dose of l-THP and l-SPD in combination with a metabolite detoxification agent, a nutritional supplement, a dietary supplement, or a carrier.

12. A method of reducing body weight and body fat in a human comprising administering to the human a dose of tetrahydroberberine (THB) and l-tetrahydropalmatine (l-THP), wherein the dose of THB and l-THP is an amount greater than 1 milligram of THB and l-THP per 1 kilogram of the human.

13. The method of claim 12 comprising administering the dose of THB and l-THP sublingually, in liquid form, in powder form, in tablet form, in a capsule, in chewing gum, in food, in a lozenge, or in a tea bag.

14. The method of claim 12 comprising administering the dose of THB and l-THP in combination with a metabolite detoxification agent, a nutritional supplement, a dietary supplement, or a carrier.

15. The method of claim 12, wherein the dose of THB and l-THP includes at least 1% THB and at least 1% l-THP by total weight of a composition in combination with a carrier.

16. A method of reducing body weight and body fat by decreasing appetite in a human comprising administering to the human an effective amount of tetrahydroberberine (THB) and l-stepholidine (l-SPD) for decreasing the human's appetite.

17. The method of claim 16, wherein the effective amount of THB and l-SPD is greater than 1 milligram of a mixture of THB and l-SPD per 1 kilogram of the human.

18. The method of claim 16 comprising administering the effective amount of THB and l-SPD sublingually, in liquid form, in powder form, in tablet form, in a capsule, in chewing gum, in food, in a lozenge, or in a tea bag.

19. The method of claim 16 comprising administering the effective amount of THB and l-SPD in combination with a metabolite detoxification agent, a nutritional supplement, a dietary supplement, or a carrier.

20. The method of claim 16, wherein the effective amount comprises at least 1% THB by total weight of a composition in combination with a carrier.

21. The method of claim 9 comprising administering the dose of l-THP and l-SPD intravenously.

22. The method of claim 12 comprising administering the dose of THB and l-THP intravenously.

23. The method of claim 16 comprising administering the effective amount of THB and l-SPD intravenously.

* * * * *